(12) United States Patent
Koren et al.

(10) Patent No.: US 9,756,313 B2
(45) Date of Patent: Sep. 5, 2017

(54) HIGH THROUGHPUT AND LOW COST HEIGHT TRIANGULATION SYSTEM AND METHOD

(71) Applicant: CAMTEK LTD., Migdal Haemek (IL)

(72) Inventors: Shimon Koren, Haifa (IL); Eldad Langmans, Haifa (IL); Menachem Regensburger, Shimshit (IL); Uri Weinar, Nahariya (IL)

(73) Assignee: CAMTEK LTD., Migdal Haemeq (IL)

( * ) Notice: Subject to any disclaimer, the term of this patent is extended or adjusted under 35 U.S.C. 154(b) by 461 days.

(21) Appl. No.: 14/284,483

(22) Filed: May 22, 2014

(65) Prior Publication Data

US 2014/0362208 A1    Dec. 11, 2014

Related U.S. Application Data

(60) Provisional application No. 61/832,866, filed on Jun. 9, 2013.

(51) Int. Cl.

| | | |
|---|---|---|
| G01B 11/22 | (2006.01) | |
| G01N 21/95 | (2006.01) | |
| H04N 13/02 | (2006.01) | |
| G01B 11/06 | (2006.01) | |
| G01N 21/956 | (2006.01) | |

(52) U.S. Cl.
CPC ..... *H04N 13/0253* (2013.01); *G01B 11/0608* (2013.01); *G01N 21/95* (2013.01); *G01N 2021/9513* (2013.01); *G01N 2021/95638* (2013.01); *G01N 2021/95676* (2013.01)

(58) Field of Classification Search
CPC ..... G01B 11/22; H04N 13/0253; G01N 21/95
See application file for complete search history.

(56) References Cited

U.S. PATENT DOCUMENTS

| | | | | |
|---|---|---|---|---|
| 5,495,337 A | * | 2/1996 | Goshorn | G01R 31/309 348/126 |
| 6,297,843 B1 | * | 10/2001 | Glew | H04N 1/32363 348/14.1 |
| 2003/0001102 A1 | * | 1/2003 | Zach | H01J 37/153 250/396 R |
| 2006/0072122 A1 | * | 4/2006 | Hu | G01B 11/2527 356/603 |
| 2013/0128247 A1 | * | 5/2013 | Khuat Duy | G03F 9/7034 355/63 |

* cited by examiner

*Primary Examiner* — Nam Pham
(74) *Attorney, Agent, or Firm* — Reches Patents

(57) ABSTRACT

A triangulation system comprising an area camera, a communication interface, a first image processing module, a second image processing module; wherein the area camera is arranged to obtain, at an acquisition rate, a stream of images of illuminated regions of an object; wherein the area camera is prevented from performing height calculations; wherein the communication interface is arranged to convey, in real time thereby in correspondence to the acquisition rate, the stream of images from the area camera to the first image processing module; wherein the first image processing module is arranged to process, in real time, the stream of images to provide first compressed information; wherein the second image processing module is arranged to process, at a non-real time image processing rate, the first compressed information to provide height information indicative of heights of at least the illuminated regions of the object.

32 Claims, 8 Drawing Sheets

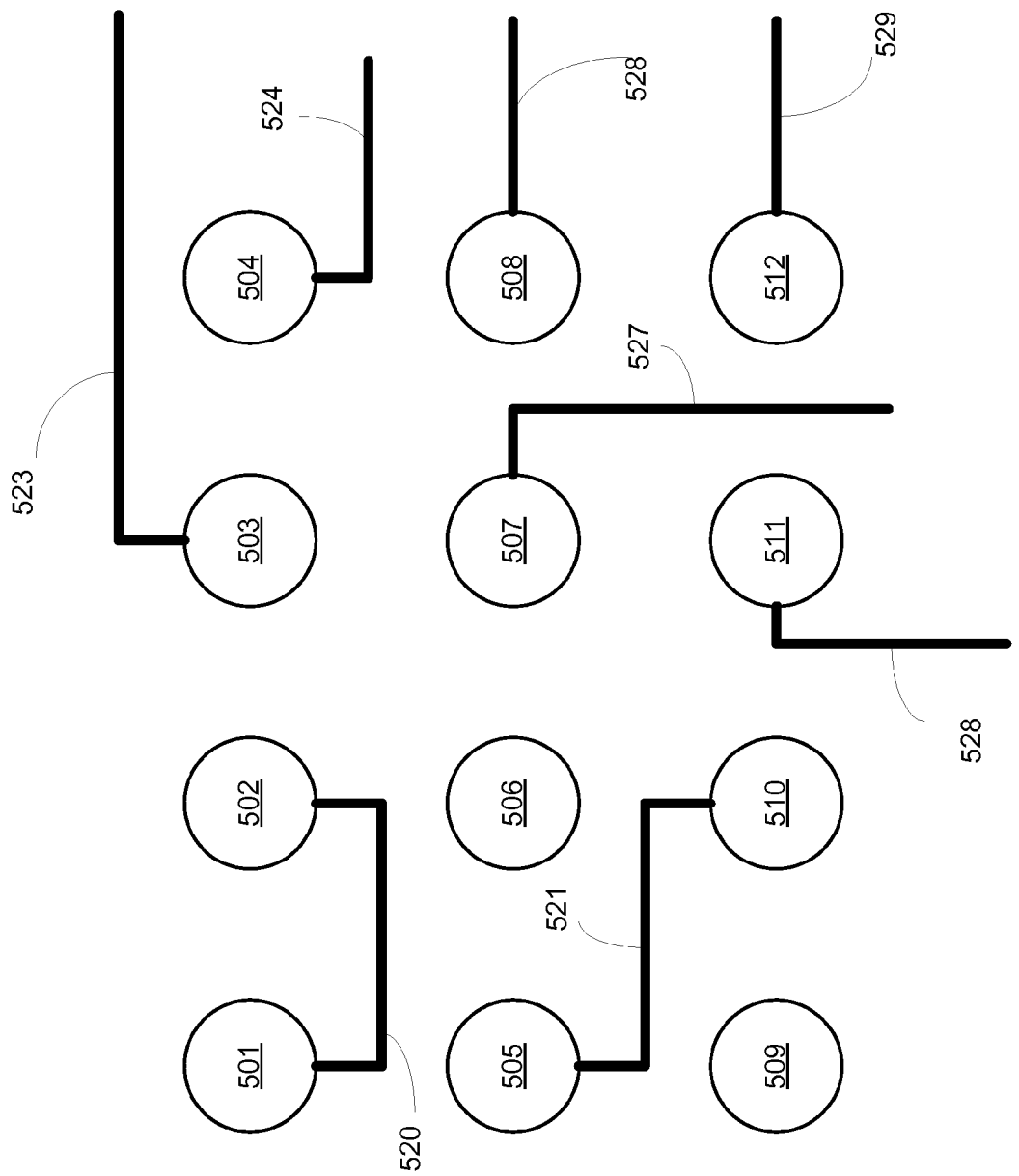

HIGH THROUGHPUT AND LOW COST HEIGHT TRIANGULATION SYSTEM AND METHOD

RELATED APPLICATIONS

This application claims priority from U.S. provisional patent Ser. No. 61/832,866 filing date Jun. 9, 2013 which is incorporated herein by reference.

BACKGROUND OF THE INVENTION

Three dimensional (3D) information about objects such as silicon wafers, printed circuit boards, reticles, flat panel display or other substrate shaped objects can be obtained in various manners that offer different tradeoffs between speed and accuracy.

Height 3D metrology requires balancing between speed and resolution/accuracy. When SEMI production worthy (full wafer metrology), fast method is required, triangulation is often the tool of choice.

Most of the industries known height triangulation systems include a dedicated 3D camera that is responsible to convert a triangulation image into 3D data.

Examples of such dedicated cameras could be found "off the shelf" from SICK-IVP ("Ranger" series), Automation Technology ("C" series), Photon Focus ("MV" series) etc. All of the mentioned examples implement either very primitive and lower accuracy 3D algorithm or a very accurate but unacceptably slow algorithm. For example, the existing dedicated 3D cameras can perform trivial, low accuracy 3D reconstruction algorithm as fast as 24K fps. On contrary, implementing high resolution accurate 3D reconstruction takes data rate to as low as 1K fps.

Other height triangulation systems implement very expensive custom-dedicated acquisition and processing designs but suffer from lack of flexibility of imaging and algorithm to meet future application needs.

Therefore, there is an imperative need of to provide flexible, cost effective and efficient height triangulation systems and methods.

SUMMARY

There are provided systems and method as illustrated in the specification and the claims.

According to an embodiment of the invention there may be provided a triangulation system that may include an area camera, a communication interface, a first image processing module, a second image processing module; wherein the area camera may be arranged to obtain, at an acquisition rate, a stream of images of illuminated regions of an object; wherein the area camera may be prevented from performing height calculations; wherein the communication interface may be arranged to convey, in real time thereby in correspondence to the acquisition rate, the stream of images from the area camera to the first image processing module; wherein the first image processing module may be arranged to process, in real time, the stream of images to provide first compressed information; wherein the second image processing module may be arranged to process, at a non-real time image processing rate, the first compressed information to provide height information indicative of heights of at least the illuminated regions of the object.

The first image processing module may include a real time frame grabber and a real time image processor.

The first image processing module may be arranged to process the stream of images by calculating first estimates of heights of the illuminated regions; wherein the first compressed information may include the first estimates of the height.

The first image processing module may be arranged to process the stream of images by: (a) calculating first estimates of heights of the illuminated regions that are responsive to locations of peaks of pixel intensity distributions that are associated with radiation from the illuminated regions; (b) calculating at least one attribute out of shape attributes and size attributes of the pixel intensity distributions, the shape and size attributes differ from the locations of the peaks; wherein the first compressed information may include the first estimates and the at least one attribute.

The system may be arranged to perform, in response to one or more attributes of the shape and size attributes that differ from the locations of the peaks, at least one out of (a) a quality measurement of a reflected signal received by the area camera when generating one or more images of the stream of images, (b) a registration of the stream of images, (c) a selection of an area to be used as a base reference surface, and (d) simultaneous metrology and defects detection of selected objects.

The shape and size attributes of a pixel intensity distribution (for example those around peaks) may be indicative of at least one out of a peak value, a width of the pixel intensity distribution, a symmetry of the pixel intensity distribution and a difference between peak and noise intensities.

The at least one of the first and second image processing modules may be arranged to determine a height of a features of the object, the feature may include multiple illuminated regions, in response to (a) first estimates of heights of the multiple illuminated regions and to (b) at least one out of shape attributes and size attributes of pixel intensity distributions of images of the multiple illuminated regions.

The second image processing module may be arranged to receive the first compressed information and to calculate second estimates of heights of the illuminated regions.

The second image processing module may be arranged to receive the first compressed information and to re-calculate one or more attribute out of the shape attributes and size attributes of the pixel intensity distributions.

The second image processing module may be arranged to receive the first compressed information and to process the first compressed information by calculating second estimates of heights of the illuminated regions; calculating at least attribute out of shape attributes and size attributes of the pixel intensity distributions, the shape and size attributes differ from the locations of the peaks.

The shape and size attributes of a pixel intensity distribution may be indicative of at least one out of a peak value, a width of the pixel intensity distribution, a symmetry of the pixel intensity distribution and a difference between peak and noise intensities.

The first image processing module may be arranged to select image portions that may include pixels indicative of the heights of the illuminated regions to provide the first compressed information.

The at least one of the first and second image processing modules may be arranged to perform image registration in response to pixel intensity distributions that are associated with radiation from one or more illuminated regions.

The at least one of the first and second image processing modules may be arranged to select from an image of an illuminated area, pixels that represent a reference surface of the object, in response to values of pixels of a pixel intensity distribution of pixels of the image.

The at least one of the first and second image processing modules may be arranged to select the pixels that represent the reference surface by differentiating between two groups of pixels that are located in proximity to each other (residing in very similar height range) but differ from each other by pixel value (by reflection intensity).

The at least one of the first and second image processing modules may be arranged to measure a dimension of a feature that may include multiple illumination areas in response to values of pixels of a pixel intensity distribution of pixels of the image.

The area camera may be prevented from calculating height information related to the heights of the illuminated regions.

The communication interface may be a CoaXPress protocol compliant communication interface.

According to an embodiment of the invention there may be provided a triangulation method that may include obtaining by an area camera, at an image acquisition rate, a stream of images of illuminated regions of an object; wherein the area camera may be prevented from performing height calculations; conveying over a communication interface, in real time thereby in correspondence to the image acquisition rate, the stream of images from the area camera to a first image processing module; real-time processing by the first image processing module, the stream of images to provide first compressed information; and non-real-time processing by a second image processing module the first compressed information to provide height information indicative of heights of at least the illuminated regions of the object.

The communication interface may be CoaXPress protocol compliant.

The real-time processing may include real time frame grabbing and real time image processing.

The real-time processing may include calculating first estimates of heights of the illuminated regions; wherein the first compressed information may include the first estimates of the height.

The real-time processing may include calculating first estimates of heights of the illuminated regions that are responsive to locations of peaks of pixel intensity distributions that are associated with radiation from the illuminated regions; and calculating at least one attribute out of shape attributes and size attributes of the pixel intensity distributions, the shape and size attributes differ from the locations of the peaks; wherein the first compressed information may include the first estimates and the at least one attribute.

The method may include performing, in response to one or more attributes of the shape and size attributes that differ from the locations of the peaks, at least one out of (a) a quality measurement of a reflected signal received by the area camera when generating one or more images of the stream of images, (b) a registration of the stream of images, (c) a selection of an area to be used as a base reference surface, and (d) simultaneous metrology and defects detection of selected objects.

The shape and size attributes of a pixel intensity distribution may be indicative of at least one out of a peak value, a width of the pixel intensity distribution, a symmetry of the pixel intensity distribution and a difference between peak and noise intensities.

The at least one of the real-time processing and the non-real time processing may include determining a height of a features of the object, the feature may include multiple illuminated regions, in response to (a) first estimates of heights of the multiple illuminated regions and to (b) at least one out of shape attributes and size attributes of pixel intensity distributions of images of the multiple illuminated regions.

The non-real time processing may include calculating second (for example—more accurate) estimates of heights of the illuminated regions.

The non-real time processing may include re-calculating one or more attribute out of the shape attributes and size attributes of the pixel intensity distributions.

The non-real time processing may include calculating second estimates of heights of the illuminated regions; and calculating at least attribute out of shape attributes and size attributes of the pixel intensity distributions, the shape and size attributes differ from the locations of the peaks.

The shape and size attributes of a pixel intensity distribution may be indicative of at least one out of a peak value, a width of the pixel intensity distribution, a symmetry of the pixel intensity distribution and a difference between peak and noise intensities.

The real-time processing may include selecting image portions that may include pixels indicative of the heights of the illuminated regions to provide the first compressed information.

The at least one of the real-time processing and the non-real time processing may include image registration in response to pixel intensity distributions that are associated with radiation from one or more illuminated regions.

The at least one of the real-time processing and the non-real time processing may include selecting from an image of an illuminated area pixels that represent a reference surface of the object, in response to values of pixels of a pixel intensity distribution of pixels of the image.

The at least one of the real-time processing and the non-real time processing may include selecting the pixels that represent the reference surface by differentiating between two groups of pixels that are located in proximity to each other but differ from each other by pixel value.

The at least one of the real-time processing and the non-real time processing may include measuring a dimension of a feature that may include multiple illumination areas in response to values of pixels of a pixel intensity distribution of pixels of the image.

The method may include preventing the area camera from calculating height information related to the heights of the illuminated regions.

BRIEF DESCRIPTION OF THE INVENTION

The present invention will be understood and appreciated more fully from the following detailed description taken in conjunction with the drawings in which:

FIG. 8 illustrates an array of bumps and multiple conductors of a substance.

DETAILED DESCRIPTION OF THE INVENTION

Because the apparatus implementing the present invention is, for the most part, composed of electronic components and circuits known to those skilled in the art, circuit details will not be explained in any greater extent than that considered necessary as illustrated above, for the understanding and appreciation of the underlying concepts of the present invention and in order not to obfuscate or distract from the teachings of the present invention.

In the following specification, the invention will be described with reference to specific examples of embodiments of the invention. It will, however, be evident that various modifications and changes may be made therein without departing from the broader spirit and scope of the invention as set forth in the appended claims.

There are provided systems and methods for height triangulation. The system and method are capable of image acquisition and processing. The system may utilize standard hardware with minimal hardware customization but allows high throughput and accuracy. The hardware may be arranged to execute instructions that allow it to execute any of the methods referred to in this application.

The system may use a standard area camera—instead of a dedicated triangulation camera. The standard area camera is standard in the sense that it is not required to perform height calculation and may merely obtain images.

The system may achieve high throughput by various means such as using a high speed data transfer protocol for triangulation system. According to an embodiment of the invention the protocol can be a CoaXPress (CXP) protocol, but may be other high speed data transfer protocol.

The CXP protocol is not used in current triangulation systems. CXP is an asymmetric high speed point to point serial communication standard for the transmission of video and still images, scalable over single or multiple coaxial cables.

According to various embodiment of the invention the system may implement dedicated height/three-dimensional algorithms for analysis of the images obtained by the area camera.

Figure 1:
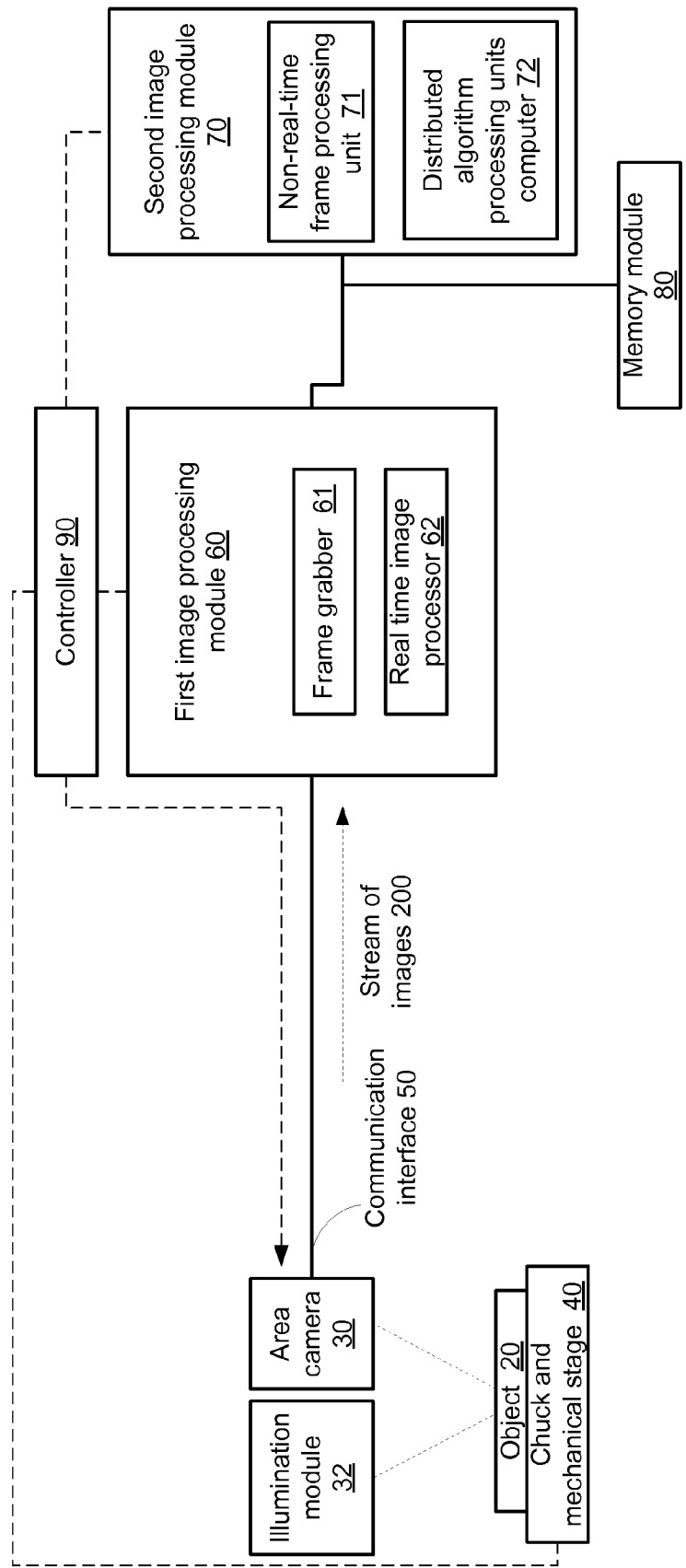
FIG. 1 illustrates a system according to an embodiment of the invention.

FIG. 1 illustrates system 11 and object 20 according to an embodiment of the invention.

System 11 includes chuck and mechanical stage 40 for supporting the object, area camera 30, illumination module 32, communication interface 50, first image processing module 60, second image processing module 70, memory module 80 and controller 90.

The controller 90 may control other components of the system 11.

The area camera 30 is arranged to obtain, at an acquisition rate, a stream of images of illuminated regions of an object. The acquisition rate can be few tens of images per second, video rate or any other rate. It is expected that each image includes thousands of pixels and even more.

The area camera 30 is not expected to extract the height information from the images and can be an ultra-fast off the shelf camera.

The communication interface 50 is arranged to convey, in real time (in correspondence to the acquisition rate) the stream of images from the area camera to the first image processing module. Accordingly—the stream of images are relayed without substantial delays and without using large buffers for compensating for gaps between the first image acquisition ate and the data transfer rate.

Figure 2:
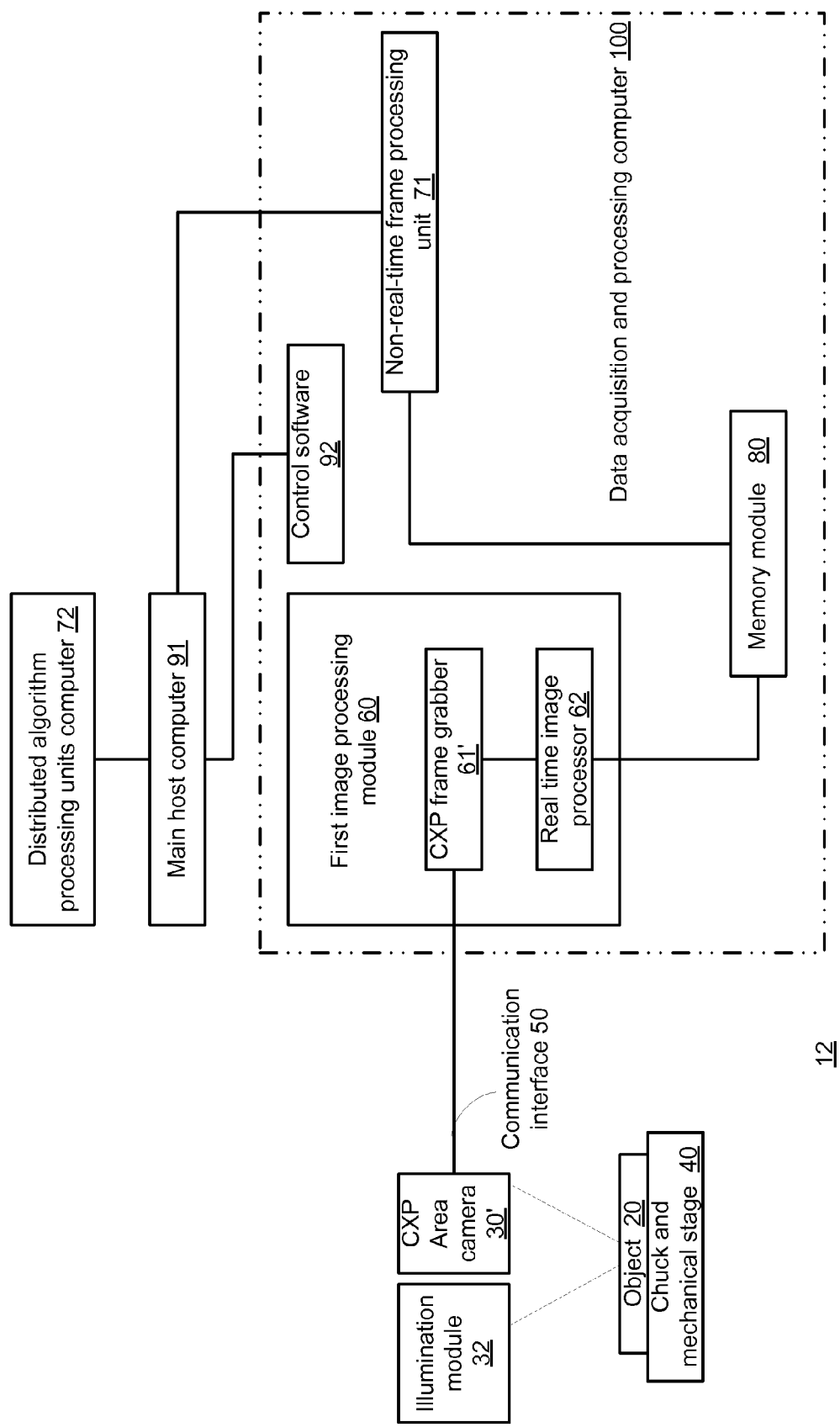
FIG. 2 illustrates a system according to an embodiment of the invention.
Figure 3:
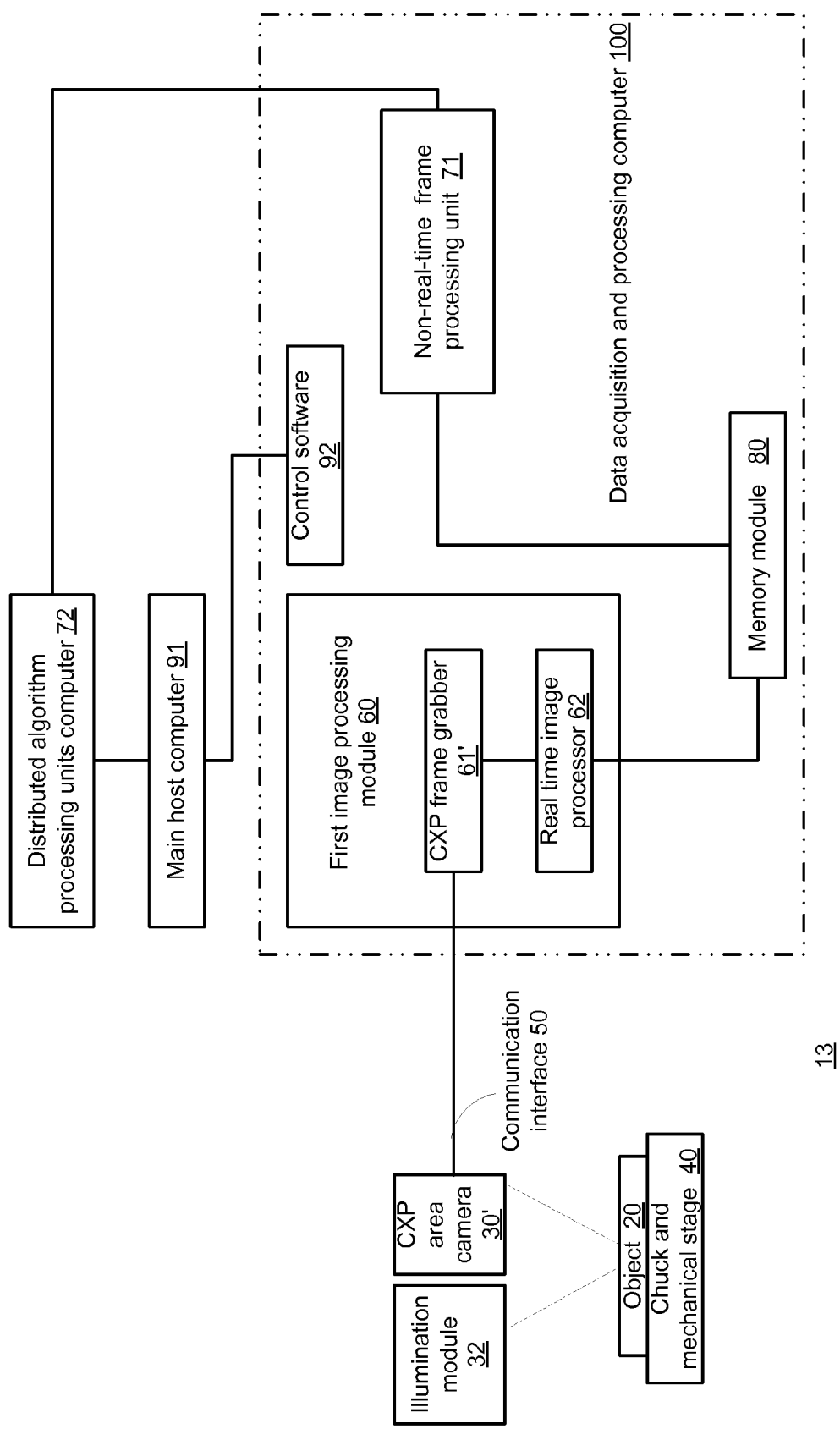
FIG. 3 illustrates a system according to an embodiment of the invention.

The communication interface 50 may be CoaXPress (CXP) compliant and may transfer large amount of data per second. There may be a variety of CXP protocols (such as CXP 6x4, CXP 12 and the like) and the system 11 may be designed to fit one or more of these CXP protocols. The area camera 30 may be equipped with a CXP interface, and the frame grabber 61 may also include a CXP interface. In FIGS. 2-3 the frame grabber is an CXP frame grabber 61' and the area camera is a CXP area camera 30'.

The first image processing module 60 is arranged to process, in real time, the stream of images to provide first compressed information. The compression applied by the first image processing module 60 may reduce (and even dramatically reduce) the amount of image information to be stored at the memory module 80. Storing the entire images sent over the communication interface 50 may be infeasible or require vast and costly memory modules. Memory module 80 can be a DRAM a VRAM or any fast accessible memory module.

The first compressed information may be formatted to facilitate further three dimensional metrology processing.

FIG. 1 illustrates the first image processing module 60 as including a CXP frame grabber 61 and a real time image processor 62.

The first image processing module 60 may allow fast direct memory access (DMA) data transfer and may be complies with PCI-E industry standard. The real time image processor 62 may be arranged to perform real time processing operations. It may include one or more FPGAs, dedicated hardware, one or more digital signal processors, and the like.

The second image processing module 70 can be referred to as a non-real time image processing module as it is not bound to the frame acquisition ate and can perform image processing operations over durations that exceed the period between acquired images.

The second image processing module 70 is arranged to process, at a non-real time image processing rate, the first compressed information to provide height information indicative of heights of at least the illuminated regions of the object.

FIG. 1 illustrates the second image processing module 70 as including non-real-time processing unit 71 and distributed algorithm processing units computer 72. It can include any combination of hardware and software components capable of performing image processing.

The non-real-times processing unit 71 may be arranged to perform any processing that requires fast but not real time performance. It may be implemented with at least one of the following architectures: multi-processor or multi-core general purpose CPU (ex. Intel Xeon architecture), a dedicated multi-core GPU (ex. NVIDIA GPU) and the like.

The distributed algorithm processing units computer 72 may be arranged to perform three dimensional 3D height post analysis, such as relative height calculation of inspected objects (bumps, pads etc.).

The memory module 80 may store first compressed information from first image processing module 60 and may store the outcome of the second image processing module 70.

FIG. 2 illustrates system 12 and object 20 according to an embodiment of the invention. FIG. 3 illustrates system 13 and object 20 according to an embodiment of the invention. Each one of system 12 and system 13 includes chuck and mechanical stage 40, CXP area camera 30', illumination module 32, communication interface 50, first image processing module 60, memory module 80, main host computer 91, non-real-time processing unit 71, distributed algorithm processing units computer 72, control software 92 and data acquisition and processing computer 100. The first image processing module 60 is illustrated as including a CXP frame grabber 61' and real time image processor 62.

A second image processing module (not shown) can include the non-real-time processing unit 61 and the distributed algorithm processing computer units 72.

The main host computer 91 may be arranged to execute a control software 92 and act as a controller.

A data and acquisition and processing computer 100 is illustrated as including the first image processing module 60, non-real-time processing unit 71, distributed algorithm processing un computer units 72 and control software 92. The non-real-time processing unit 71 may access the memory module 80 and be accessed by the main host computer 91. The distributed algorithm processing computer units 72 may be accessed by the main host computer 91.

System 13 differs from system 12 by having the non-real-time processing unit 71 accessed by the distributed algorithm processing computer units 72 and not by the main host computer 91.

In both systems 12 and 13, during the metrology process of an object a line of light may scan the object and the area camera samples light reflected from illuminated line shaped regions of the object. The location of the line within the image (see, for example, distance D 130 between line 111 and the bottom of image 110 of FIG. 4) is indicative of the height of the illuminated image. Higher illuminated regions will be represented by lines that are closer to the top of the image. U.S. Pat. No. 8,363,229 illustrates a height triangulation system that includes a camera that obtains such images and outputs height information.

The image may include n columns by m rows of pixels.

Figure 4:
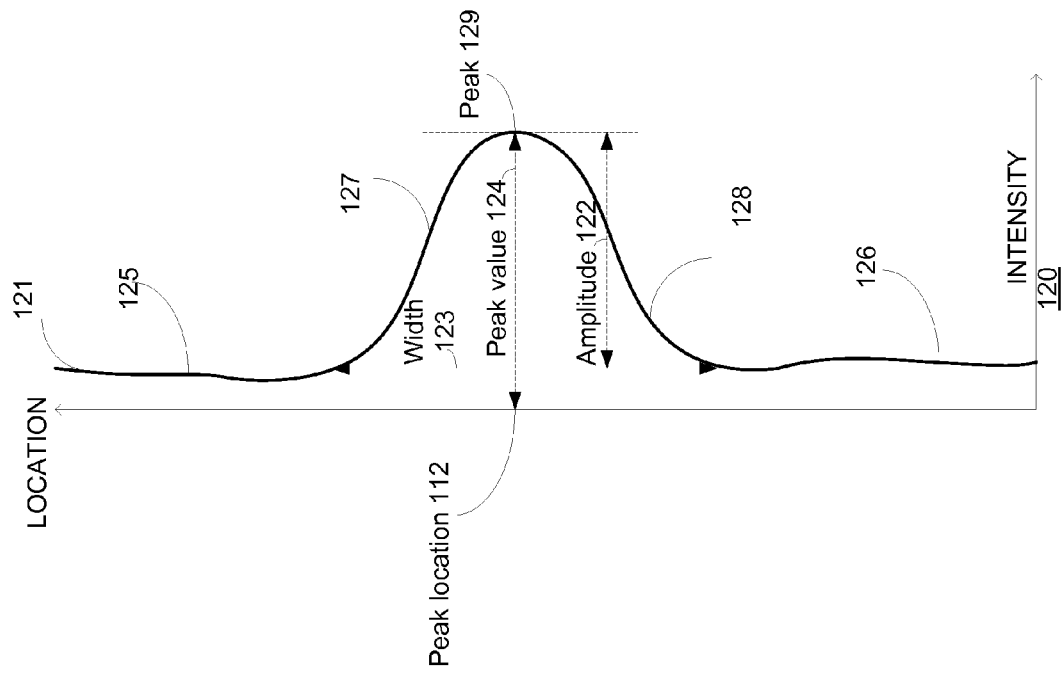
FIG. 4 illustrates an image and a curve indicative of pixel values along a pixel column of the image according to an embodiment of the invention.
Figure 4:
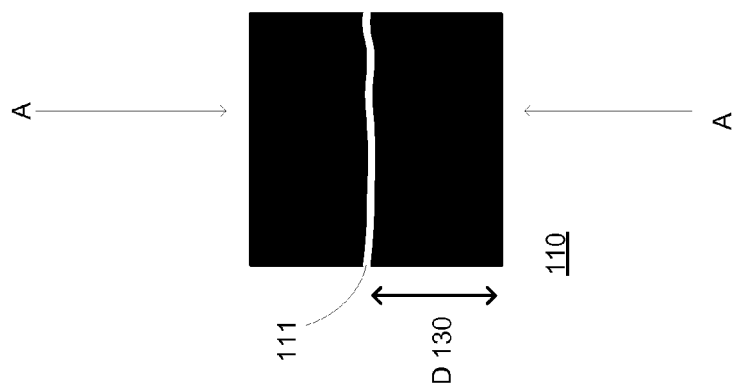

FIG. 4 illustrates an image 110 that includes a bright line 111 that represents a reflection from an illuminated region (usually a region illuminated by a strip of light) and a black background. It is noted that the actual image includes more than just black and white pixels and includes pixels of a variety of pixel levels. The values of the pixels of the image provide pixel intensity distributions that are associated with radiation from the illuminated regions. FIG. 4 includes graph 120 that in turn includes a curve that illustrates intensities of pixels of one column of image. For n columns there are n curves that may differ from each other.

Graph 120 includes a curve 121 and various attributes associated with the curve 121. The curve 121 includes a central lobe that includes first and second portions 126 and 127, peak 129 and background portions 125 and 126 surrounding first and second portions 126 and 127.

FIG. 4 also illustrates a peak location attribute 112 and various shape and size attributes related to curve 121 such as the peak value 124, an amplitude 124 of the peak 129 (difference between peak value 124 and value of background pixels), and lobe width 123. Additional attributes may include a symmetry attribute indicative of the symmetry of the curve 121 (or of the lobe alone). The peak location attribute 112 can be calculated at sub-pixel resolution.

Referring back to FIG. 1—at least one out of the first image processing module 60 and the second image processing module 70 may calculate one or more of the attributes mentioned above.

The first image processing module 60 may calculate one or more attributes. The second image processing module 70 can re-calculate the one or more attributes, calculate at least one attribute not calculated by the first image processing module 60 or can perform both.

At least one of the first and second image processing modules 60 and 70 may perform one or more error correction processes such as but not limited to dark noise response correction DSNU, pixels linear response correction PRNU, and flat field correction (FFC).

Figure 5:
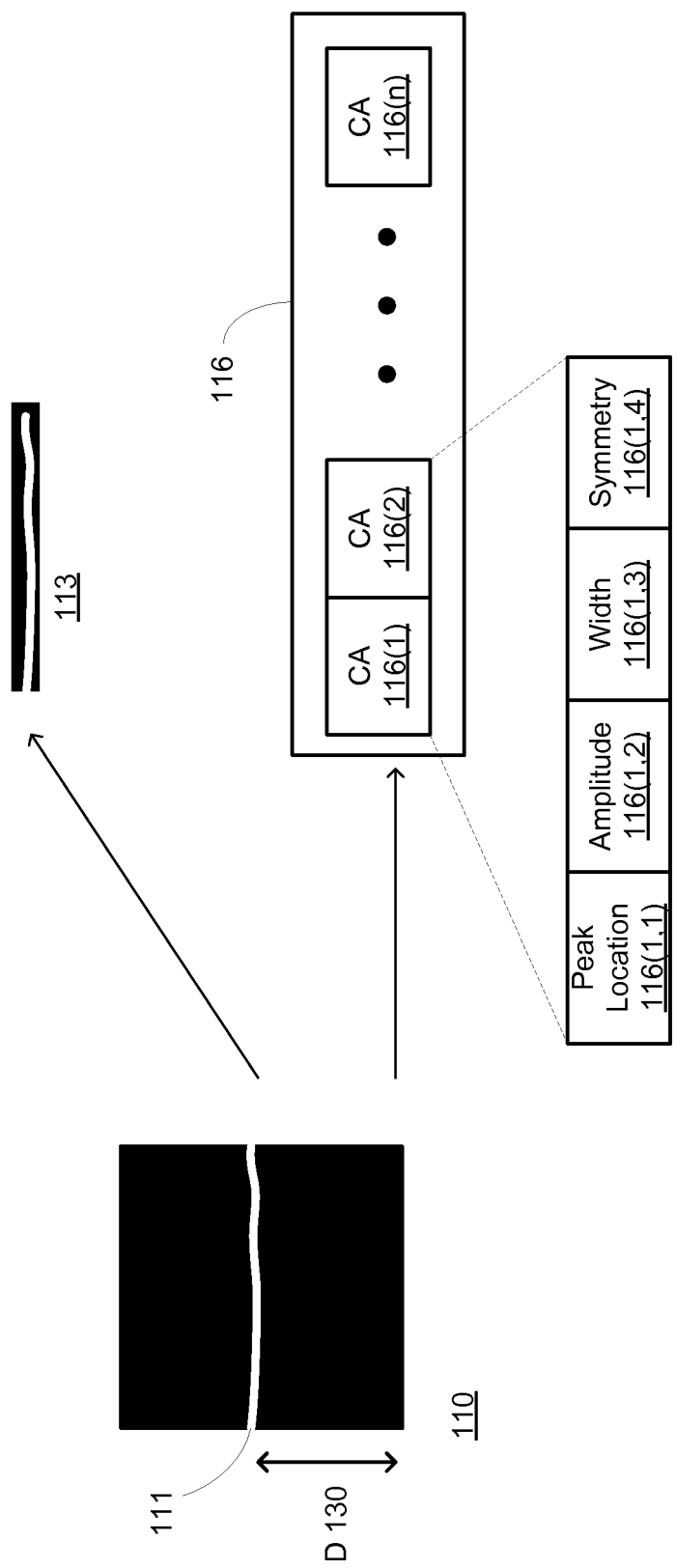
FIG. 5 illustrates an image and first compressed information according to an embodiment of the invention.
Figure 6:
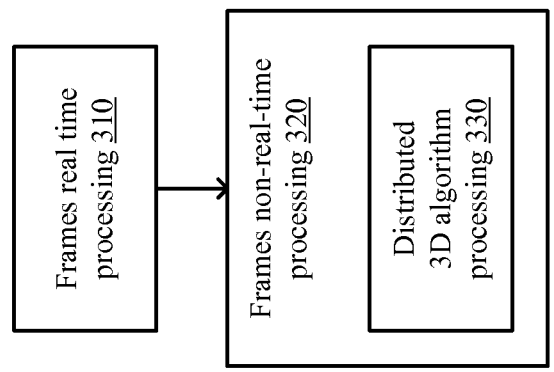
FIG. 6 illustrates a method according to an embodiment of the invention.

FIG. 5 illustrates image 110 and various types of first compressed information according to various embodiments of the invention.

The first compressed information may be raw information such a selected portion 113 of the image 110. The selected portion 113 is selected by the first image processing module 60 to include pixels that include information about the illuminated regions. For example it may include the pixels that their intensity forms the lobes (or at least a majority of the lobes) of the pixel intensity distributions of the image 110.

The first compressed information may include at least partially processed height information.

FIG. 5 illustrates the first compressed information as including a metadata vector 116 that includes a metadata unit per each of the n columns of each image—CA 116(1)-116(n). Each metadata unit includes attributes such as peak location attribute (height estimation), amplitude attribute, width attribute and symmetry attribute. Any other (or additional) shape and/or size attribute of the may be included. FIG. 5 illustrates CA 116(1) of a first column of image 110 as including peak location attribute 116(1,1), amplitude attribute 116(1,2), width attribute 116(1,3) and symmetry attribute 116(1,4).

FIG. 3 illustrates method 300 according to an embodiment of the invention. The method may include the following stages:

a. Frames (real time) "RT" processing (310)—the processing that synchronized with frames acquisition rate. The RT processing comprises one or some (application dependent) of following operations:

i. DSNU/PRNU (dark signal and photon response non-uniformity) that comes to compensate for area camera fixed pattern noise (a.k.a. FPN) and general optical field non-uniformity (such as illumination etc.).

ii. Data Reduction (a.k.a. CDR), comprises 3D triangulation signal dedicated lossless compression of raw frame data. The compression method is based on fast identification of the 3D relevant signal on each image column, suppressing non-relevant dark regions of each column and accompanying each column data with meta-data to allow future decompression and processing.

iii. RT peak detector comprising sub-pixel resolution detection of a peak at each column. The peak detection is pre-configured to extract the peak of interest according the application requirements (such as "strongest peak", "first peak", "second peak" etc.).

iv. The peak detector processing "converts" each raw frame of 'n' columns by 'm' rows (of given bit depth) to a series of 'n' entries where each entries comprises the sub-pixel peak position and the quality identifier (or identifiers) of a given peak (for example, amplitude, width, symmetry etc.).

v. The output series values can be represented as floating point and/or integer and/or coded to fixed point convention or integer value according to the accuracy requirements. The RT peak detector is coupled with frames acquisition requirements and therefore is implemented in FPGA, DSP, ASIC or any other dedicated RT HW.

b. Frames non-real-time processing (320)—also referred to as post-processing (320)—the processing that not-synchronized with frames acquisition rate. The non-synchronized processing allows flexible implementation and virtually unlimited precision. The non-RT (unsynchronized) processing comprises one or some (application and RT-processing step dependent) of following operations:

i. DSNU/PRNU (dark signal and photon response non-uniformity) that comes to compensate for area camera fixed pattern noise (a.k.a. FPN) and general optical field non-uniformity (such as illumination etc.). This step comes to complete/replace the RT-based DSNU/PRNU correction process.

ii. Unsynchronized peak detector process comprising sub-pixel resolution detection of a peak at each column (exactly as RT-peak detector) but is not limited with an implementation by frame rate constraints and therefore not limited with dedicated HW implementation. The unsynchronized peak detector comes to complete/replace the RT-based peak detector process (application dependent).

1. The peak detection is pre-configured to extract the peak of interest according the application requirements (such as "strongest peak", "first peak", "second peak" etc.).
   2. The peak detector implements (but not limited) convolution, derivative, signals de-composition etc. technique.
   3. The peak detector processing "converts" each raw frame of 'n' columns by 'm' rows (of given bit depth) to a series of 'n' entries where each entry comprises the sub-pixel peak position and the quality identifier of a given peak (for example, amplitude, width, symmetry etc.). The output series values can be represented as floating point and/or integer and/or coded to fixed point convention or integer value according to the accuracy requirements.

c. The non-real time processing (320) may include distributed 3D algorithm processing (330)—Process the 3D frames, as combined out of lines generated by peak detector processing (ether RT or unsynchronized).

i. Performing a 3D data segmentation based on 3D frame data and identify pre-defined 3D structures vs. reference data.

ii. Computing height of each pre-defined 3D structure object based on 3D frame data and statistical analysis.

iii. Applying height offset with respect to optical distortion correction using pre-calibrated data.

According to an embodiment of the invention the series of 'n' sub-pixel position of the reflection represents a distance from the sensor (Height). See distance D 130 of FIG. 4 and peak location attribute 116(1,1) of FIG. 5.

Instead of using only the peak location attribute for triangulation, the at least one attributes (such as those illustrated in FIG. 5) may be used (by any one of systems 11, 12 and 13) for at least some of the following purposes: (a) quality measure of the reflected signal, (b) registration, (c) selective base surface usage, and (d) simultaneous metrology and defects detection of selected objects.

Quality measure of the reflected signal—the additional features may be used to estimate the quality of the reflection. For example, lower reflection intensity on the top of a sphere may indicate a non-optimal reflection angle for measurement. Using the signal shape features gives the ability to selectively choose the reflections to use\discard or alternatively give a score\weight to each of the "height" measurements thus increasing the reliability of the overall measurement when taking into account the entire reflection surface from the object. For example—when illuminating a bump (of substantially homogenous reflection) it is expected that the intensity of the reflection (and/or symmetry of the pixel distribution) increases towards the peak of the bump. This intensity may be used for better estimating a height of a feature. When a bump is inspected the pixels that have greater amplitude and/or better symmetry are provided a higher weight that those of lower amplitude and/or lower symmetry.

Registration—the additional features and specifically the amplitude information is much more suited for the purpose of registering the acquired image (a set of 'm' sequential reflection lines comprising 'n' columns of data) to the "real world" or some reference image. The amplitude image contains information regarding the surface's reflectance and not just height. This means that even for surfaces with the same height we are able to distinguish between the two types of surfaces. This leads to an image containing much more geometrical information which is more suited for the purpose of registration the image \ objects in the image. Registration may be done using any of the known image registration methods (for example—intensity based, feature based, frequency domain, etc.). For example—the objects to be inspected may include features that differ from each other by their reflective index even when they are of substantially the same height. These changes in the reflective indexes may be utilized for searching for features of various types (bumps, conductors) for alignment purposes. For example—conductors can have a high reflective index (higher than the reflective index of bumps) and they may be better suited for alignment and/or registration processes. FIG. 8 illustrates an array of bumps 501-512 and a group of conductors 520-529 that differ from each other and may be used for registration.

Selective base surface usage—the process of measuring an objects height consists of measuring the reflection from the "Top" of the object relative to the reflection of some "base reference" surface. Using the additional signal features it is possible to segment (using any number of segmentation algorithms, such as those using multivariate statistics models, density based, connectivity based, etc.') the surface region into "sub" surfaces having similar signal properties. This segmentation enables specific selection of the "base reference" sub surface.

The objects to be inspected may include features that differ from each other by their reflective index even when they are of substantially the same height. Conductors that have different reflective index that of the base surface can be detected and their pixels can be ignored when searching for the base surface. For example—the conductors 520-529 of FIG. 8 may be positioned above a background surface 500. There may be a slight height difference between the conductors 520-529 and the background surface 500 and in order to clearly select pixels related to one of these areas the difference in their reflectance index (and hereby amplitude) may be taken into account.

Simultaneous metrology and surface detection of selected objects—similar to the above segmentation approach, it is possible to use the signal features (as mentioned above) data to compose a single\multi dimension image\signal containing information regarding the characteristics of the reflecting surface. Thus, it is also possible to create a reference image\images from which we can infer the nominal behavior of the surface in this single\multi-dimensional image\signal.

Obtaining various attributes, in addition to just height may assist in measuring feature dimensions using information obtained by a single scan of the object.

This, together with a proper registration sequence can be used to simultaneously perform:

Surface inspection of the surfaces and/or target objects in the image.

Height measurement of objects.

Lateral dimensions metrology.

This parallelization leads to increase in machine throughput.

The single\multi-dimensional information is also helpful in correct classification of various types of defect classes.

Figure 7:
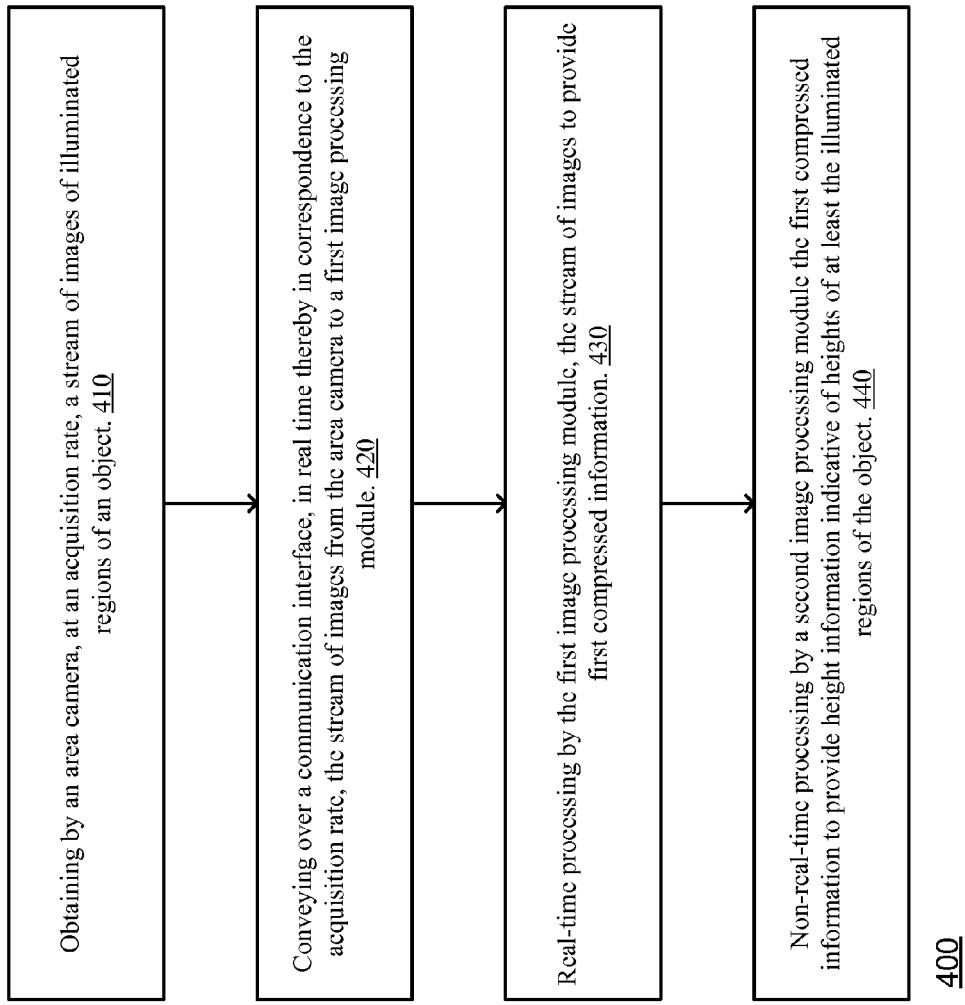
FIG. 7 illustrates a method according to an embodiment of the invention.

FIG. 7 illustrates method 400 according to an embodiment of the invention.

Method 400 may start by stage 410 of obtaining by an area camera, at an acquisition rate, a stream of images of illuminated regions of an object.

The area camera may be prevented from performing height estimations.

Stage 410 may be followed by stage 420 of conveying over a communication interface, in real time thereby in correspondence to the acquisition rate, the stream of images from the area camera to a first image processing module. The communication interface may be CoaXPress protocol compliant.

Stage 420 may be followed by stage 430 of real-time processing by the first image processing module, the stream of images to provide first compressed information.

Stage 430 may be followed by stage 440 of non-real-time processing by a second image processing module the first compressed information to provide height information indicative of heights of at least the illuminated regions of the object.

Stage 430 may include at least one out of: (a) real time frame grabbing, (b) real time image processing, (c) calculating first estimates of heights of the illuminated regions, wherein the first compressed information comprises the first estimates of the height, (d) calculating first estimates of heights of the illuminated regions that are responsive to locations of peaks of pixel intensity distributions that are associated with radiation from the illuminated regions, (e) calculating at least one attribute out of shape attributes and size attributes of the pixel intensity distributions, the shape and size attributes differ from the locations of the peaks, wherein the first compressed information comprises the first estimates and the at least one attribute. Shape and size attributes of a pixel intensity distribution are indicative of at least one out of a peak value, a width of the pixel intensity distribution, a symmetry of the pixel intensity distribution and a difference between peak and noise intensities; (f) selecting image portions that comprises pixels indicative of the heights of the illuminated regions to provide the first compressed information.

Stage 440 may include at least one out of (a) calculating second estimates of heights of the illuminated regions, (b) re-calculating one or more attribute out of the shape attributes and size attributes of the pixel intensity distributions, (c) calculating second estimates of heights of the illuminated regions, (d) calculating at least attribute out of shape attributes and size attributes of the pixel intensity distributions, the shape and size attributes differ from the locations of the peaks, wherein shape and size attributes of a pixel intensity distribution may be indicative of at least one out of a peak value, a width of the pixel intensity distribution, a symmetry of the pixel intensity distribution and a difference between peak and noise intensities; (e) post processing by a distributed algorithm processing units computer.

At least one of stages 430 and 440 may include at least one of the following: (a) determining a height of a features of the object, the feature comprising multiple illuminated regions, in response to (i) first estimates of heights of the multiple illuminated regions and to (ii) at least one out of shape attributes and size attributes of pixel intensity distributions of images of the multiple illuminated regions; (b) performing image registration in response to pixel intensity distributions that are associated with radiation from one or more illuminated regions; (c) selecting from an image of an illuminated area pixels that represent a reference surface of the object, in response to values of pixels of a pixel intensity distribution of pixels of the image; (d) selecting the pixels that represent the reference surface by differentiating between two groups of pixels that are located in proximity to each other but differ from each other by pixel value; (e) measuring a dimension of a feature that comprises multiple illumination areas in response to values of pixels of a pixel intensity distribution of pixels of the image.

The invention may also be implemented in involving a computer program for running on a computer system, at least including code portions for performing steps of a method according to the invention when run on a programmable apparatus, such as a computer system or enabling a programmable apparatus to perform functions of a device or system according to the invention. The computer program may cause the storage system to allocate disk drives to disk drive groups.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system.

The computer program may be stored internally on a non-transitory computer readable medium. All or some of the computer program may be provided on computer readable media permanently, removably or remotely coupled to an information processing system. The computer readable media may include, for example and without limitation, any number of the following: magnetic storage media including disk and tape storage media; optical storage media such as compact disk media (e.g., CD-ROM, CD-R, etc.) and digital video disk storage media; nonvolatile memory storage media including semiconductor-based memory units such as FLASH memory, EEPROM, EPROM, ROM; ferromagnetic digital memories; MRAM; volatile storage media including registers, buffers or caches, main memory, RAM, etc.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the broader spirit and scope of the invention as set forth in the appended claims.

Those skilled in the art will recognize that boundaries between the functionality of the above described operations are merely illustrative. The functionality of multiple operations may be combined into a single operation, and/or the functionality of a single operation may be distributed in additional operations. Moreover, alternative embodiments may include multiple instances of a particular operation, and the order of operations may be altered in various other embodiments.

Thus, it is to be understood that the architectures depicted herein are merely exemplary, and that in fact many other architectures can be implemented which achieve the same functionality. In an abstract, but still definite sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

However, other modifications, variations, and alternatives are also possible. The specifications and drawings are, accordingly, to be regarded in an illustrative rather than in a restrictive sense.

The word "comprising" does not exclude the presence of other elements or steps then those listed in a claim. It is understood that the terms so used are interchangeable under appropriate circumstances such that the embodiments of the invention described herein are, for example, capable of operation in other orientations than those illustrated or otherwise described herein.

Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe.

Thus, these terms are not necessarily intended to indicate temporal or other prioritization of such elements. The mere fact that certain measures are recited in mutually different claims does not indicate that a combination of these measures cannot be used to advantage.

We claim:

1. A triangulation system comprising an area camera, a communication interface, a first image processing module, a second image processing module;
    wherein the area camera is arranged to obtain, at an acquisition rate, a stream of images of illuminated regions of an object; wherein the area camera is prevented from performing height calculations;
    wherein the communication interface is arranged to convey, in real time thereby in correspondence to the acquisition rate, the stream of images from the area camera to the first image processing module;
    wherein the first image processing module is arranged to process, in real time, the stream of images to provide first compressed information, by:
    (a) calculating first estimates of heights of the illuminated regions that are responsive to locations of peaks of pixel intensity distributions that are associated with radiation from the illuminated regions;
    (b) calculating at least one attribute out of shape attributes and size attributes of the pixel intensity distributions, the shape and size attributes differ from the locations of the peaks;
    wherein the first compressed information comprises the first estimates and the at least one attribute;
    wherein the second image processing module is arranged to process, at a non-real time image processing rate, the first compressed information to provide height information indicative of heights of at least the illuminated regions of the object.

2. The system according to claim 1 wherein the first image processing module comprises a real time frame grabber and a real time image processor.

3. The system according to claim 1 wherein the system is arranged to perform, in response to one or more attributes of the shape and size attributes that differ from the locations of the peaks, at least one out of (a) a quality measurement of a reflected signal received by the area camera when generating one or more images of the stream of images, (b) a registration of the stream of images, (c) a selection of an area to be used as a base reference surface, and (d) simultaneous metrology and defects detection of selected objects.

4. The system according to claim 1 wherein shape and size attributes of a pixel intensity distribution are indicative of at least one out of a peak value, a width of the pixel intensity distribution, a symmetry of the pixel intensity distribution and a difference between peak and noise intensities.

5. The system according to claim 1 wherein at least one of the first and second image processing modules is arranged to determine a height of a features of the object, the feature comprising multiple illuminated regions, in response to (a) first estimates of heights of the multiple illuminated regions and to (b) at least one out of shape attributes and size attributes of pixel intensity distributions of images of the multiple illuminated regions.

6. The system according to claim 1 wherein the second image processing module is arranged to receive the first compressed information and to calculate second estimates of heights of the illuminated regions.

7. The system according to claim 1 wherein the second image processing module is arranged to receive the first compressed information and to re-calculate one or more attribute out of the shape attributes and size attributes of the pixel intensity distributions.

8. The system according to claim 1 wherein the first image processing module is arranged to select image portions that comprise pixels indicative of the heights of the illuminated regions to provide the first compressed information.

9. The system according to claim 1 wherein at least one of the first and second image processing modules is arranged to perform image registration in response to pixel intensity distributions that are associated with radiation from one or more illuminated regions.

10. The system according to claim 1 wherein at least one of the first and second image processing modules is arranged to select from an image of an illuminated area, pixels that represent a reference surface of the object, in response to values of pixels of a pixel intensity distribution of pixels of the image.

11. The system according to claim 1 wherein the at least one of the first and second image processing modules is arranged to select the pixels that represent a reference surface by differentiating between two groups of pixels that are located in proximity to each other but differ from each other by pixel value.

12. The system according to claim 1 wherein at least one of the first and second image processing modules is arranged to measure a dimension of a feature that comprises multiple illumination areas in response to values of pixels of a pixel intensity distribution of pixels of the image.

13. The system according to claim 1 wherein the area camera is prevented from calculating height information related to the heights of the illuminated regions.

14. The system according to claim 1 wherein the communication interface is a CoaXPress protocol compliant communication interface.

15. A triangulation system comprising an area camera, a communication interface, a first image processing module, a second image processing module;
wherein the area camera is arranged to obtain, at an acquisition rate, a stream of images of illuminated regions of an object; wherein the area camera is prevented from performing height calculations;
wherein the communication interface is arranged to convey, in real time thereby in correspondence to the acquisition rate, the stream of images from the area camera to the first image processing module;
wherein the first image processing module is arranged to process, in real time, the stream of images to provide first compressed information;
wherein the second image processing module is arranged to process, at a non-real time image processing rate, the first compressed information to provide height information indicative of heights of at least the illuminated regions of the object, by
(a) calculating second estimates of heights of the illuminated regions;
(b) calculating at least attribute out of shape attributes and size attributes of the pixel intensity distributions, the shape and size attributes differ from the locations of the peaks.

16. The system according to claim 15 wherein shape and size attributes of a pixel intensity distribution are indicative of at least one out of a peak value, a width of the pixel intensity distribution, a symmetry of the pixel intensity distribution and a difference between peak and noise intensities.

17. A triangulation method comprising:
obtaining by an area camera, at an image acquisition rate, a stream of images of illuminated regions of an object; wherein the area camera is prevented from performing height calculations;
conveying over a communication interface, in real time thereby in correspondence to the image acquisition rate, the stream of images from the area camera to a first image processing module;
real-time processing by the first image processing module, the stream of images to provide first compressed information; wherein the real-time processing of the stream of images comprises: calculating first estimates of heights of the illuminated regions that are responsive to locations of peaks of pixel intensity distributions that are associated with radiation from the illuminated regions; and calculating at least one attribute out of shape attributes and size attributes of the pixel intensity distributions, the shape and size attributes differ from the locations of the peaks; wherein the first compressed information comprises the first estimates and the at least one attribute; and
non-real-time processing by a second image processing module the first compressed information to provide height information indicative of heights of at least the illuminated regions of the object.

18. The method according to claim 17 wherein the communication interface is CoaXPress protocol compliant.

19. The method according to claim 17 wherein the real-time processing comprises real time frame grabbing and real time image processing.

20. The method according to claim 17 wherein shape and size attributes of a pixel intensity distribution are indicative of at least one out of a peak value, a width of the pixel intensity distribution, a symmetry of the pixel intensity distribution and a difference between peak and noise intensities.

21. The method according to claim 17 comprising performing, in response to one or more attributes of the shape and size attributes that differ from the locations of the peaks at least one out of (a) a quality measurement of a reflected signal received by the area camera when generating one or more images of the stream of images, (b) a registration of the stream of images, (c) a selecting of an area to be used as a base reference surface, and (d) simultaneous metrology and defects detection of selected objects.

22. The method according to claim 17 wherein at least one of the real-time processing and the non-real time processing comprises determining a height of a features of the object, the feature comprising multiple illuminated regions, in response to (a) first estimates of heights of the multiple illuminated regions and to (b) at least one out of shape attributes and size attributes of pixel intensity distributions of images of the multiple illuminated regions.

23. The method according to claim 17 wherein the non-real time processing comprises calculating second estimates of heights of the illuminated regions.

24. The method according to claim 17 wherein the non-real time processing comprises re-calculating one or more attribute out of the shape attributes and size attributes of the pixel intensity distributions.

25. The method according to claim 17 wherein the real-time processing comprises selecting image portions that comprise pixels indicative of the heights of the illuminated regions to provide the first compressed information.

26. The method according to claim 17 wherein at least one of the real-time processing and the non-real time processing comprises image registration in response to pixel intensity distributions that are associated with radiation from one or more illuminated regions.

27. The method according to claim 17 wherein at least one of the real-time processing and the non-real time processing comprises selecting from an image of an illuminated area pixels that represent a reference surface of the object, in response to values of pixels of a pixel intensity distribution of pixels of the image.

28. The method according to claim 17 wherein at least one of the real-time processing and the non-real time processing comprises selecting the pixels that represent a reference surface by differentiating between two groups of pixels that are located in proximity to each other but differ from each other by pixel value.

29. The method according to claim 17 wherein at least one of the real-time processing and the non-real time processing comprises measuring a dimension of a feature that comprises multiple illumination areas in response to values of pixels of a pixel intensity distribution of pixels of the image.

30. The method according to claim 17 comprising preventing from the area camera calculating height information related to the heights of the illuminated regions.

31. A triangulation method comprising:
   obtaining by an area camera, at an image acquisition rate, a stream of images of illuminated regions of an object; wherein the area camera is prevented from performing height calculations;
   conveying over a communication interface, in real time thereby in correspondence to the image acquisition rate, the stream of images from the area camera to a first image processing module;
   real-time processing by the first image processing module, the stream of images to provide first compressed information; and
   non-real-time processing by a second image processing module the first compressed information to provide height information indicative of heights of at least the illuminated regions of the object;
   wherein the non-real time processing comprises:
   calculating second estimates of heights of the illuminated regions; and
   calculating at least attribute out of shape attributes and size attributes of the pixel intensity distributions, the shape and size attributes differ from the locations of the peaks.

32. The method according to claim 31 wherein shape and size attributes of a pixel intensity distribution are indicative of at least one out of a peak value, a width of the pixel intensity distribution, a symmetry of the pixel intensity distribution and a difference between peak and noise intensities.

* * * * *